United States Patent [19] [11] 3,994,929
Allen et al. [45] Nov. 30, 1976

[54] PRODUCTION OF 2,2-DISUBSTITUTED PROPIOLACTONES
[75] Inventors: Robert P. Allen; Hugh J. Hagemeyer, Jr., both of Longview, Tex.
[73] Assignee: Eastman Kodak Company, Rochester, N.Y.
[22] Filed: June 2, 1975
[21] Appl. No.: 583,338

Related U.S. Application Data
[63] Continuation-in-part of Ser. No. 303,570, Nov. 11, 1972, Pat. No. 3,891,679.

[52] U.S. Cl. .......................................... 260/343.9
[51] Int. Cl.² .................................... C07D 305/12
[58] Field of Search ................................ 260/343.9

[56] References Cited
UNITED STATES PATENTS
3,907,829   9/1975   Holmes et al. ................... 260/343.9

Primary Examiner—Henry R. Jiles
Assistant Examiner—C. Jaisle
Attorney, Agent, or Firm—Edward R. Weber; Daniel B. Reece, III

[57] ABSTRACT

The present invention relates to a process for the manufacture of 2,2-disubstituted propiolactones via the pyrolysis of methylene diisoalkylate in the vapor phase over a fixed bed catalyst system. The reaction of the invention is as follows:

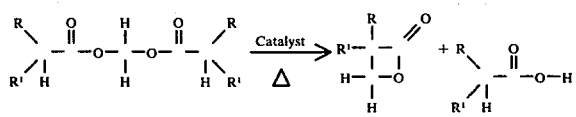

wherein R is alkyl of from 1 to 4 carbon atoms and R¹ is alkyl of from 1 to 4 carbon atoms or phenyl. The catalyst comprises an oxide of a metal selected from the group Ag, U, Zn, Ti, Zr, Th, Ta, Nb, Mo, W, and Sn on a suitable support. A preferred catalyst is the metal oxide-silica gel complex which results from heating the calcined residue of a salt of a metal selected from the group consisting of Ta, Ti, Nb and Zr supported upon a silica gel in the presence of nitrogen and steam at a temperature of from about 650° C. to about 1000° C. The process is operable at temperatures from about 240° C. to about 360° C. with contact times ranging from about 0.1 second to about 30.0 seconds. The gaseous ester feed may, if desired, be diluted with an inert gas such as nitrogen and the reactor may be run at atmospheric, or superatmospheric pressure.

39 Claims, No Drawings

PRODUCTION OF 2,2-DISUBSTITUTED PROPIOLACTONES

This is a continuation-in-part of application Serial No. 303,570, filed November 11, 1972, now U.S. Pat. No. 3,891,679, patented 6-24-75.

The present invention relates to a process for preparing 2,2-disubstituted propiolactones by the pyrolysis of a methylene diisoalkylate in the vapor phase over a fixed bed catalyst.

2,2-Disubstituted propiolactones are useful in the polymer industry as staring material for synthetic resins and synthetic fibers. They are also useful in the pharmaceutical industry and have heretofore been prepared by a variety of methods. For example, in U.S. Pat. No. 2,356,459, there is described a well-known method for preparing 2,2-disubstituted propiolactones by the addition reaction of dimethyl ketene and formaldehyde. The known methods for the manufacture of 2,2-disubstituted propiolactones, however, can be practiced on a commercial scale only with difficulties and result in economic disadvantages.

It is therefore an object of our invention to provide a simplified method for the preparation of 2,2-disubstituted propiolactones.

It is another object to provide a one-step method for the preparation of 2,2-disubstituted propiolactones.

Other objects of the invention will become apparent from a consideration of the specification and claims of this application.

The reaction of this invention is believed to proceed according to the following formula

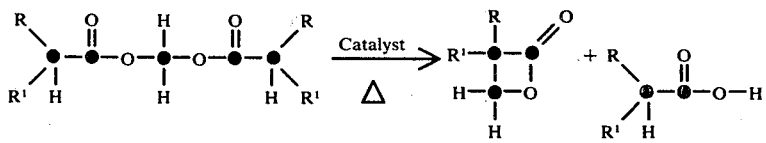

wherein R is alkyl of from 1–4 carbon atoms and $R^1$ is alkyl of 1–4 carbon atoms or phenyl. The catalyst comprises an oxide of a metal selected from the group Ag, U, Zn, Ti, Zr, Th, Ta, Nb, Mo, W, and Sn on a suitable support. A preferred catalyst is the metal oxide-silica gel complex which results from heating the calcined residue of a salt of a metal selected from the group consisting of Ta, Ti, Nb and Zr supported upon a silica gel in the presence of nitrogen and steam at a temperature of from about 650° C. to about 1000° C. A particularly effective catalyst comprises a steam treated tantalum oxide-silica gel complex wherein the silica gel utilized has a relatively low surface area and a relatively large pore volume.

There is no known prior art which discloses or predicts this reaction process. Known methods to produce pivalolactone by transesterification require the presence of the neopentyl structure to effect ring closure as illustrated below:

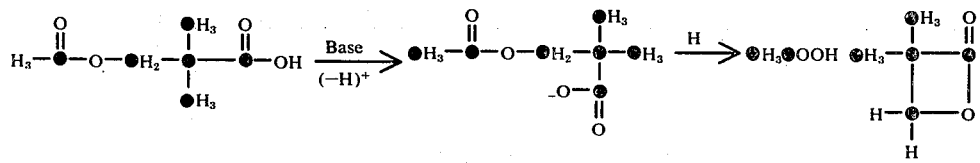

No chemical mechanism is known which would suggest that a "neo" structure could be formed from the methylene diisoalkylate starting material and subsequently rearranged to form 2,2-disubstituted propiolactone. Likewise, no literature is known which would suggest any method in which methylene esters could be cyclized to form β-lactones. It was, therefore, quite unexpected that 2,2-disubstituted propiolactones could be produced from methylene diesters in a one-step catalyzed vapor phase process. The actual mechanics of the invention are still unknown. However, a theory on the bond shifting that occurs is illustrated by the following equation:

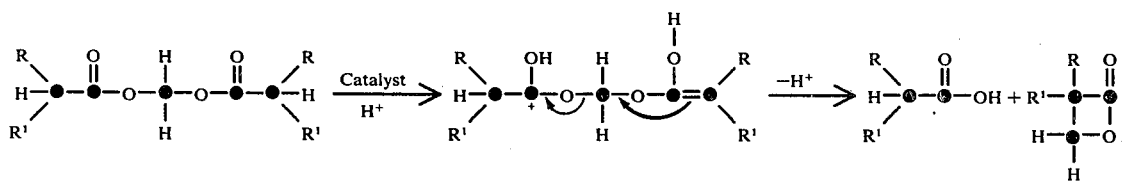

As discussed hereinabove, in the process of the instant invention a gem diester having the formula

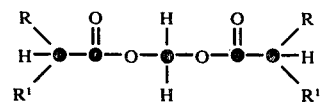

is pyrolyzed in the vapor phase over a solid catalyst at a temperature of from about 240° C. to about 360° C. with a contact time of from about 0.1 second to about 30 seconds. The gaseous ester feed may, if desired, be diluted with an inert gas to facilitate feeding of the reactants, control of contact time, etc. The reaction may be conducted at atmospheric, subatmospheric or superatmospheric pressure. Reduced pressure may be desirable to facilitate vaporization of the reactants and/or products.

Reaction products comprise a 2,2-disubstituted propiolactone having the formula

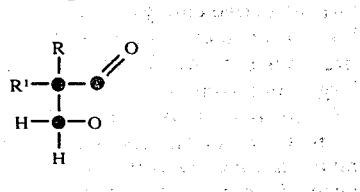

and an organic acid having the formula

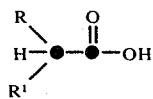

In all the above formulas R can be any straight or branched chain, saturated alkyl containing 1–4 carbon atoms and $R^1$ may be any straight or branched chain saturated alkyl containing 1–4 carbon atoms or phenyl.

Suitable diester feed materials include methylene diisobutyrate, methylene bis(dibutyl acetate), methylene bis($\alpha$-methyl hexanoate), methylene bis(methyl phenyl acetate), methylene bis(butyl phenyl acetate), and the like.

The reaction occurs in the presence of a catalyst comprising an oxide of a metal selected from the group Ag, U, Zn, Ti, Ar, Th, Ta, Nb, Mo, W, and Sn on a suitable support. A preferred catalyst is the metal oxide-silica gel complex which results from heating the calcined residue of a salt of a metal selected from the group consisting of Ta, Ti, Nb and Zr supported upon a silica gel in the presence of nitrogen and steam at a temperature of from about 650° C. to about 1000° C. An especially effective catalyst consists of the metal oxide-silica gel complex which results from heating the calcined residue of a tantalum salt supported on a relatively low surface area, large pore volume, silica gel, such as Davison Chemical Company's G-59, in the presence of nitrogen and steam at a temperature of from about 650° C. to about 1000° C. Particularly good results are obtained when the calcined residue is heated at a temperature of from about 730° C. to about 780° C. for a period of from about 3 to about 6 hours.

A common method or regeneration of catalysts is to burn carbonaceous material from the catalyst at temperatures of up to about 550° C. The 550° C. temperature is selected since above about 600° C. silica gel begins to sinter and lose its structural properties. Experimental work has shown that heating at 550° C. has very little effect on catalyst activity of the heavy metal oxide catalyst in similar reactions. It was therefore quite surprising that heating a heavy metal oxide-silica gel catalyst to temperatures of from about 650° C. to about 1000° C. in the presence of steam produced a highly selective catalyst with long life which could be readily rengereated.

The supported metal oxide catalysts of the instant invention are conveniently formed by mixing one of their water-soluble salts such as a nitrate, acetate, oxalate, or ammonium salt with a support and then removing the water by evaporation. Calcining the material in nitrogen at from about 400° C. to about 600° c. and then in air at from about 400° C. to about 600° C. produces the desired supported metal oxide. A preferred temperature range for the calcining steps is from about 500° C. to about 550° C. If desired, the metal oxide can be precipitated directly upon the support by use of a suitable chemical reaction. Any of the known inert support materials can be utilized to support the heavy metal oxide. Typical useful supports are silica, alumina, celatom, pumice, and silicon carbide. A relatively low surface area (less than about 400 square meters per gram) and large pore volume (greater than about 0.8 cc per gram) silica gel has been found to be effective. A preferred silica gel has a surface area of from about 340 square meters per gram to about 360 square meters per gram and a pore volume of from about 1.00 cc. per gram to about 1.25 cc. per gram. Silica gel having a surface area of about 340 square meters per gram and a pore volume of about 1.15 cc. per gram has been found to be particularly effective.

In a preferred embodiment the metal is selected from the group consisting of Ta, Ti, Nb and Zr and silica gel is selected as the support. The silica gel supported calcined metal oxide is then heated in a nitrogen steam mixture at a temperature of from about 650° C. to 1000° C. until the desired metal oxide-silica gel complex is formed, usually from about 2 to about 10 hours. The nitrogen is used to facilitate more uniform heat distribution. Good results have been obtained with $N_2$ to $H_2O$ ratios of from about 0.1:1 to about 10:1. An exact description of the catalyst complex is not available. It is best characterized by the unique, greatly improved properties it exhibits when compared to analogous catalysts or those prepared by alternate methods.

During the heat treating cycle (650°–1000° C.) the relationship of time of treatment to temperature may be varied considerably. Higher temperatures require shorter treatment times and vice versa. An excellent catalyst has been obtained by steam treatment in nitrogen at 760°–780° C. for 4 to 6 hours. It is essential, however, that the final heat treatment be in the 650°–1000° C. range. A more practical measurement to obtain a catalyst of greatest activity, selectivity and life span is based on the volume of the solid catalyst. When the catalyst being treated at 650°–1000° C. has been reduced in volume by not less than 5 percent and not more than 20 percent, the desired catalyst complex has been attained.

In a particularly preferred embodiment of the subject invention an aqueous solution of tantalum oxalate is used as a convenient source of soluble tantalum for the deposition of tantalum oxide on the silica gel. The catalyst is prepared by soaking the silica gel in an aqueous solution of the tantalum oxalate, removing the water by evaporation, calcining the solid residue in nitrogen at a temperature of about 550° C. for 1-½ hours and then in air at a temperature of about 550° C. for 1-½ hours, and heating the resultant silica gel-tantalum oxide mix in a nitrogen steam mixture at a temperature of from about 650° C. to about 1000° C. for 2 to 8 hours.

Optimum process conditions such as contact time, temperature, amount of diluent gas and feed composition will vary for the different metal oxide-silica gel complex catalysts. In general, the best results are obtained at a contact time of from about 0.5 to about 10.0 seconds, although this may vary over a much broader range, such as from about 0.1 second to about 30.0 seconds.

Preferably the temperature selected will be sufficient to insure vaporization of the reactants and the products. The process may be operated at temperatures of from about 240° C. to about 360° C.

Particularly preferred reaction conditions for maximum yield with the preferred catalyst will consist of a contact time of about 2 seconds, use of nitrogen diluent gas, and an operating temperature of from about 290° C. to about 310° C. Maximum conversion will occur under the same operating conditions if the temperature is raised to about 340° C.

The reaction may be carried out at atmospheric, subatmospheric, or superatomspheric pressure. If desired, an inert diluent gas may be utilized to facilitate feeding of the reactants, control of contact time, etc. Good results are obtained at atmospheric pressure using an inert diluent gas, usually in a molar ratio of gas to organic feed of from about 1:10 to about 20:1, preferably about 1:1 to 6:1, and most preferably from about 2:1 to 4:1. A suitable inert diluent gas is any gas which does not react with either the reactants or the products under the conditions of the reaction, such as $N_2$, argon, helium, gaseous hydrocarbons and compounds which are readily vaporized such as benzene.

The process of the invention is illustrated in greater detail by the following examples which are all conducted at atmospheric pressure, but it will be understood that these examples are not intended to limit the invention in any way and obvious modifications will occur to those skilled in the art. All examples are run at atmospheric pressure in a 2 foot by 22 mm. Vycor reactor.

EXAMPLE 1

This example illustrates the preparation of a steam treated tantalum oxide on silica gel catalyst.

A tantalum oxalate solution containing 10.32 grams tantalum is diluted to 300 milliliters with water and 100 grams of G-59 silica gel is added. The mixture is allowed to equilibrate at room temperature for 18 hours and then taken to dryness on a steam bath. The dried catalyst is heated to 550° C. with a nitrogen sweep to decompose the salt, swept with an air stream to promote oxidation, and then treated with nitrogen and steam at 765°–780° C. for 6 hours. The catalyst appears to have decreased in volume by approximately 10 percent.

EXAMPLE 2

This example illustrates the preparation of pivalolactone with high conversion of methylene diisobutyrate.

Methylene diisobutyrate is fed to a pyrolysis tube which contains a tantalum oxide on silica gel catalyst as prepared in Example 1 and inert packing. The temperature of the catalyst bed and inert material is maintained at 340 ± 10° C., insuring that no liquid material will impinge on the catalyst surface. Nitrogen is used as a diluent and sweep gas. With a contact time of 2 seconds, pivalolactone is produced in 18 percent conversion and 31 percent yield.

EXAMPLE 3

This example illustrates the preparation of pivalolactone with high yield based on methylene diisobutyrate consumed.

Methylene diisobutyrate is fed to a pyrolysis tube which contains a tantalum oxide on silica gel catalyst as prepared in Example 1 and inert packing. The temperature of the catalyst bed and inert material is maintained at 295 ± 5° C., insuring that no liquid material will impinge on the catalyst surface. Nitrogen is used as a diluent and sweep gas. With a contact time of 2 seconds, pivalolactone is produced in 9 percent conversion and 42 percent yield.

EXAMPLE 4

This example illustrates the catalyst dependence of the reaction.

Methylene diisobutyrate is fed to a pyrolysis tube packed with Vycor chips. At 335 ± 10° C. the methylene diisobutyrate is recovered unchanged.

The invention has been described in detail with particular reference to preferred embodiments thereof, but it will be understood that variations and modifications can be effected within the spirit and scope of the invention as described hereinabove.

We claim:

1. A process for producing a 2,2-disubstituted propiolactone having the formula

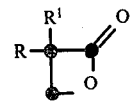

whereby a methylene diester having the formula

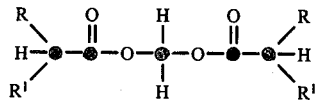

wherein R is alkyl having 1–4 carbon atoms and $R^1$ is alkyl of from 1–4 carbon atoms or phenyl, is pyrolyzed at a temperature of from about 240° C. to about 360° C. in the presence of an oxide of a metal selected from the group Ag, U, Zn, Ti, Zr, Th, Ta, Nb, Mo, W, and Sn supported on an inert support.

2. The process of claim 1 wherein the methylene diester is selected from the group consisting of methylene diisobutyrate, methylene bis(dibutyl acetate), methylene bis(α-methyl hexanoate), methylene bis(methyl phenyl acetate), methylene bis(butyl phenyl acetate).

3. The process of claim 1 wherein the support material is selected from the group consisting of silica, alumina, celatom, pumice, and silicon carbide.

4. The process of claim 1 wherein the catalyst is formed by mixing a water-soluble salt of the selected heavy metal with the selected support, removing the water by evaporation, and subsequently calcining the material at a temperature of from about 400° C. to about 600° C.

5. The process of claim 4 wherein the calcining takes place at a temperature of from about 500° C. to about 550° C.

6. The process of claim 1 wherein the reaction is conducted at a temperature of from about 290° C. to about 310° C.

7. The process of claim 1 wherein the reaction is conducted at atmospheric pressure.

8. A process for producing pivalolactone whereby methylene diisobutyrate is pyrolyzed at a temperature of from about 240° C. to about 360° C. in the presence of an oxide of a metal selected from the group Ag, U, Zn, Ti, Zr, Th, Ta, Nb, Mo, W, and Sn Supported on an inert support.

9. The process of claim 8 wherein the supporting material is selected from the group consisting of silica, alumina, celatom, pumice, and silicon carbide.

10. The process of claim 8 wherein the catalyst is formed by mixing a water-soluble salt of the selected heavy metal with the selected support, removing the water by evaporation, and subsequently calcining the material at a temperature of from about 400° C. to about 600° C.

11. The process of claim 10 wherein the calcining takes place at a temperature of from about 500° C. to about 550° C.

12. The process of claim 8 wherein the reaction is conducted at a temperature of from about 290° C. to about 310° C.

13. The process of claim 8 wherein the reaction is conducted at atmospheric pressure.

14. A process for producing 2,2-disubstituted propiolactone having the formula

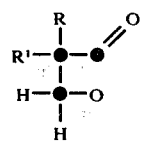

whereby a methylene diester having the formula

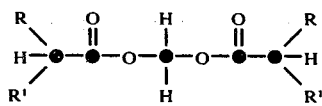

wherein R is alkyl having 1–4 carbon atoms and R¹ is alkyl of from 1–4 carbon atoms or phenyl, is pyrolyzed at a temperature of from about 240° C. to about 360° C. in the presence of a catalyst consisting of the metal oxide-silica gel complex which results from heating the calcined residue of a mixture of silica gel and a salt or oxide of a metal selected from the group consisting of tantalum, titanium, niobium and zirconium to a temperature of from about 650° C. to about 1000° C. in the presence of water vapor.

15. The process of claim 14 wherein the methylene diester is selected from the group consisting of methylene diisobutyrate, methylene bis(dibutyl acetate), methylene bis(α-methyl hexanoate), methylene bis(methyl phenyl acetate), methylene bis(butyl phenyl acetate).

16. The process of claim 14 wherein the catalyst is formed by mixing a water-soluble salt of the selected heavy metal with silica gel, removing the water by evaporation, and subsequently calcining the material at a temperature of from about 400° C. to about 600° C.

17. The process of claim 16 wherein the calcining takes place at a temperature of from about 500° C. to about 550° C.

18. The process of claim 14 wherein the calcined residue is heated, in the presence of water vapor, to a temperature of from about 730° C. to about 780° C.

19. The process of claim 18 wherein the calcined residue is heated, in the presence of water vapor, for a period of from about 3 to about 6 hours.

20. The process of claim 18 wherein the calcined residue is heated, in the presence of water vapor, to a temperature of from about 760° C. to about 780° C.

21. The process of claim 20 wherein the calcined residue is heated, in the presence of water vapor, for a period of from about 4 to about 6 hours.

22. The process of claim 14 wherein the process is conducted at atmospheric pressure.

23. The process of claim 14 wherein the silica gel has a relatively low surface area and a relatively large pore volume.

24. The process of claim 23 wherein the silica gel has a surface area of less than about 400 m² per gram and a pore volume of greater than about 0.8 cc. per gram.

25. The process of claim 24 wherein the silica gel has a surface area of from about 340 to about 360 m²/gm. and a pore volume of from about 1.00 to about 1.25 cc. per gram.

26. The process of claim 14 wherein the pyrolysis is conducted at a temperature of from about 290° C. to about 310° C.

27. A process for producing pivalolactone whereby methylene diisobutyrate is pyrolyzed at a temperature of from about 240° C. to about 360° C. in the presence of the metal oxide-silica gel complex whic results from heating the calcined residue of a mixture of silica gel and a salt or oxide of a metal selected from the group consisting of tantalum, titanium, niobium and zirconium to a temperature of from about 650° C. to about 1000° C. in the presence of water vapor.

28. The process of claim 27 wherein the catalyst is formed by mixing a water-soluble salt of the selected heavy metal with silica gel, removing the water by evaporation, and subsequently calcining the material at a temperature of from about 400° C. to about 600° C.

29. The process of claim 28 wherein the calcining takes place at a temperature of from about 500° C. to about 550° C.

30. The process of claim 27 wherein the calcined residue is heated, in the presence of water vapor, to a temperature of from about 730° C. to about 780° C.

31. The process of claim 30 wherein the calcined residue is heated, in the presence of water vapor, for a period of from about 3 to about 6 hours.

32. The process of claim 30 wherein the calcined residue is heated, in the presence of water vapor, to a temperature of from about 760° C. to about 780° C.

33. The process of claim 32 wherein the calcined residue is heated, in the presence of water vapor, for a period of from about 4 to about 6 hours.

34. The process of claim 27 wherein the pyrolysis is conducted at atmospheric pressure.

35. The process of claim 27 wherein the pyrolysis is conducted at reduced pressure.

36. The process of claim 27 wherein the silica gel has a relatively low surface area and a relatively large pore volume.

37. The process of claim 36 wherein the silica gel has a surface area of less than about 400 m² per gram and a pore volume of greater than about 0.8 cc. per gram.

38. The process of claim 37 wherein the silica gel has a surface area of from about 340 to about 360 m²/gm. and a pore volume of from about 1.00 to about 1.25 cc. per gram.

39. The process of claim 27 wherein the pyrolysis is conducted at a temperature of from about 290° C. to about 310° C.

* * * * *